United States Patent
Nho et al.

(10) Patent No.: US 12,295,991 B2
(45) Date of Patent: May 13, 2025

(54) HEMOGLOBIN DERIVATIVE CO-CONJUGATED WITH FATTY ACID-LINKED PEG AND ALKOXY PEG AS A BLOOD SUBSTITUTE

(71) Applicant: SunBio, Inc., Gyeonggi-do (KR)

(72) Inventors: Kwang Nho, Gyeonggi-do (KR);
Minjung Ahn, Gyeonggi-do (KR);
Changmin Hyun, Gyeonggi-do (KR);
JungHun Lee, Gyeonggi-do (KR)

(73) Assignee: SunBio, Inc., Gyeonggi-do (KR)

( * ) Notice: Subject to any disclaimer, the term of this patent is extended or adjusted under 35 U.S.C. 154(b) by 0 days.

(21) Appl. No.: 17/357,374

(22) Filed: Jun. 24, 2021

(65) Prior Publication Data
US 2021/0401949 A1    Dec. 30, 2021

Related U.S. Application Data

(60) Provisional application No. 63/044,579, filed on Jun. 26, 2020.

(51) Int. Cl.
*A61K 38/42* (2006.01)
*A61K 47/54* (2017.01)
*A61K 47/60* (2017.01)

(52) U.S. Cl.
CPC ............ *A61K 38/42* (2013.01); *A61K 47/542* (2017.08); *A61K 47/545* (2017.08); *A61K 47/60* (2017.08)

(58) Field of Classification Search
None
See application file for complete search history.

(56) References Cited

U.S. PATENT DOCUMENTS

| | | | | |
|---|---|---|---|---|
| 8,021,858 | B2 * | 9/2011 | Vandegriff | A61K 47/60 435/69.6 |
| 2004/0072729 | A1 * | 4/2004 | Kwang | A61K 38/42 514/17.7 |
| 2010/0075379 | A1 * | 3/2010 | Vandegriff | A61K 47/60 435/69.6 |

FOREIGN PATENT DOCUMENTS

| | | | |
|---|---|---|---|
| EP | 1465643 | * | 1/2008 |
| EP | 1465643 B1 | | 1/2008 |
| KR | 10-2000-0061432 | * | 10/2000 |
| KR | 10-2000-0061432 A | | 10/2000 |
| WO | 2004-081053 | * | 9/2004 |

OTHER PUBLICATIONS

Premont et al. ("Essential Role of Hemoglobin βCys93 in Cardiovascular Physiology". Physiology (Bethesda). Jul. 1, 2020; 35(4):234-243. Published online Jun. 3, 2020. doi: 10.1152/physiol.00040.2019; https://www.ncbi.nlm.nih.gov/pmc/articles/PMC7474257/).*
Vijayaraghavan et al. Suitability of polymer materials for production of pulmonary microparticles using a PGSS supercritical fluid technique: Thermodynamic behaviour of fatty acids, PEGs and PEG-fatty acids Author links open overlay panel. International Journal of Pharmaceutics vol. 438, Issues 1-2, Nov. 15.*
Svergun et al. Solution structure of poly(ethylene) glycol-conjugated hemoglobin revealed by small-angle X-ray scattering: implications for a new oxygen therapeutic. Biophys J. Jan. 1, 2008;94(1):173-81. doi: 10.1529/biophysj.107.114314. Epub Sep. 7, 2007. PMID: 17827244; PMCID: PMC2134876. https://www.ncbi.nlm.nih.g.*
Taguchi et al. Comparison of the Pharmacokinetic Properties of Hemoglobin-Based Oxygen Carriers. J Funct Biomater. Mar. 18, 2017;8(1):11. doi: 10.3390/jfb8010011. PMID: 28335469; PMCID: PMC5371884. https://www.ncbi.nlm.nih.gov/pmc/articles/PMC5371884/.*
Vandegriff et al. Hemospan: design principles for a new class of oxygen therapeutic. Artif Organs. Feb. 2009;33(2):133-8. doi: 10.1111/j.1525-1594.2008.00697.x. PMID: 19178457. https://pubmed.ncbi.nlm.nih.gov/19178457/.*
Written Opinion, International Patent Application No. PCT/KR2021/003530, mailed Jul. 1, 2021, 6 pages.
International Search Report, International Patent Application No. PCT/KR2021/003530, mailed Jul. 1, 2021, 5 pages.

* cited by examiner

*Primary Examiner* — Maury A Audet
(74) *Attorney, Agent, or Firm* — Casimir Jones, S.C.; Robert A. Goetz

(57) ABSTRACT

The invention relates to hemoglobin derivative, particularly hemoglobin which is co-conjugated with both fatty acid-linked polyethylene glycol (FA-PEG) derivatives and alkoxy polyethylene glycol (alkoxy-PEG) derivatives, and a method for making such hemoglobin derivative. Various embodiments of the invention include crosslinked hemoglobin which is co-conjugated with both FA-PEG derivatives and alkoxy-PEG derivatives. Such hemoglobin derivative according to the invention exhibit non-toxicity and extended intravascular retention time.

13 Claims, No Drawings

HEMOGLOBIN DERIVATIVE CO-CONJUGATED WITH FATTY ACID-LINKED PEG AND ALKOXY PEG AS A BLOOD SUBSTITUTE

CROSS REFERENCE TO RELATED APPLICATION

This application claims the benefit of U.S. Prov. Appl. 63/044,579, filed Jun. 26, 2020, which is incorporated by reference herein in its entirety.

FIELD OF THE INVENTION

The present invention relates to a hemoglobin derivative utilized as hemoglobin-based oxygen carrier (HBOC). More specifically, the present invention relates to a hemoglobin derivative in which hemoglobin (Hb) or crosslinked hemoglobin (xHb) is co-conjugated with fatty acid-PEG (FA-PEG) derivatives and alkoxy-PEG derivatives.

BACKGROUND OF THE INVENTION

The need for a safe and readily available blood substitute which has the purpose of treating patients and soldiers in need of blood transfusion in emergency situations where there is no blood available on site has been well-recognized for several decades. A trauma center is one medical setting in which a blood substitute that can be administered immediately without blood type matching when a blood transfusion is greatly needed. A blood substitute is also useful in utilization in general medical situations, such as anemia, brain strokes, perioperative procedures, and organ preservation.

Blood substitutes that have been developed can be categorized as: i) perfluorocarbon-based solutions, ii) liposome-encapsulated hemoglobin, iii) polymer vesicle-encapsulated hemoglobin, iv) a hemoglobin-based oxygen carrier (HBOC) and v) red blood cells produced by stem cell technology.

Among blood substitutes, HBOCs have been so far most successful in that several different formulations of HBOCs have entered clinical trials and generated valuable clinical data. Among some of the HBOCs which have entered current clinical trials, one of the HBOCs, Hemopure™ by HbO₂ Therapeutics of Massachusetts, USA, has gained marketing approval in South Africa under certain conditions. HBOCs are hemoglobin-based in that hemoglobin is the active ingredient comprising the oxygen carrying capability. The hemoglobins used in several HBOC candidates are human, bovine, recombinant, or transgenic hemoglobins and the like. The HBOC which has entered the market, Hemopure™, is of a bovine source. There are various sources of hemoglobin. However, it seems that the mode of modification of hemoglobin, not the source of hemoglobin, is an important factor in deciding the clinical outcome related to HBOCs.

Native hemoglobin has been known to be unsuitable to be used as a blood substitute due to its tendency to dissociate into smaller subunits and cause rapid elimination through kidneys, which makes it unacceptably short-lived and toxic. Modification of native hemoglobin has been pursued by applying diverse technologies with the goal of stabilizing the hemoglobin structure as well as increasing the total molecular weight so as to increase intravascular half-life.

Modification of hemoglobin has been explored by many developers and can be categorized in general terms as follows: i) intra-molecular crosslinking between subunits of hemoglobin, ii) polymerization of hemoglobin, iii) surface modification of hemoglobin, or any combination thereof.

Intra-molecular crosslinking of hemoglobin was devised in order to stabilize the intrinsically labile tetrameric structure of hemoglobin that consists of two α subunits and two β subunits. The four subunits make up one molecule of hemoglobin, but have a tendency to dissociate into individual subunits that become non-functional and lose the oxygen-carrying capability. To prevent such dissociation, a small-sized chemical reagent, such as bis(3,5-dibromosalicyl) fumarate or bis(3,5-dibromosalicyl) succinate, was introduced into the cleft between subunits, resulting in two subunits being linked together via the reagent, thus preventing the dissociation of the Hb tetramer. Intra-molecular crosslinking of hemoglobin has been known in the art, as pioneered in a publication titled "Diaspirins That Cross-Link β Chains of Hemoglobin: Bis(3,5-dibromosalicyl) Succinate and Bis(3,5-dibromosalicyl) Fumarate" (Walder, J. A. et al., Biochemistry, Vol 18, No 20, 4265-4270, 1979).

Polymerization of hemoglobin has been employed to increase the molecular weight of a final product as a few molecules of hemoglobin are linked together via a conjugating chemical reagent, and thus this method has been termed polymerization of hemoglobin. One notable example is Hemopure™ by Biopure, Inc. which uses glutaraldehyde as the polymerizing reagent.

Surface modification of hemoglobin was devised in ways to increase the total molecular weight of the modified hemoglobin as well as to coat the surface of hemoglobin with a non-immunogenic polymer or other materials of a significant weight and useful function. As an example, polyethylene glycol (PEG) modified hemoglobin (Hb), abbreviated PEG-Hb, was developed by a process in which multiple strands of PEG are covalently conjugated to the surface amines of hemoglobin. For the conjugation, a variety of PEG derivatives can be used to react with ε-amines of surface lysines of hemoglobin. The conjugation chemistry employs the mechanism of nucleophilic substitution reaction in which a PEG having an electrophilic functional group is attacked by the nucleophilic amines of hemoglobin, which results in a conjugation reaction taking place between the PEG and the nitrogen of amine, while the functional group of a PEG derivative is detached as a leaving group. Depending on the type of PEG derivative utilized, the resultant linkage between the PEG and the amine of Hb can be an amide, carbamate, carbonate, ester, ether, or urethane bond. The first inventions of PEG-Hb were disclosed in U.S. Pat. Nos. 5,234,903, and 5,386,014 (Nho et al), and many PEG-Hb patents have been registered thereafter.

The following cited patents are all related to PEG-Hb, which differ in terms of conjugation chemistry, oxygen affinity or delivery capability, and stabilization technology. However, none of the prior patents or literature disclosed the composition of a fatty acid-linked PEG-conjugated Hb for use as a blood substitute.

U.S. Pat. No. 5,234,903 (Nho et al., 1993) titled "Chemically modified hemoglobin as an effective, stable non-immunogenic red blood cell substitute" disclosed a method for making a chemically modified hemoglobin comprising hemoglobin conjugated to polyalkylene oxide by urethane linkage and having a p50 greater than 20 mmHg, wherein the chemically modified hemoglobin in the polyalkylene oxide is poly(ethylene glycol).

U.S. Pat. No. 5,386,014 (Nho et al., 1995) titled "Chemically modified hemoglobin as an effective, stable, non-immunogenic red blood cell substitute" disclosed a method of producing a chemically modified hemoglobin comprising: (i) reducing and deoxygenating bovine hemoglobin; and (ii) conjugating the reduced, deoxygenated bovine hemoglobin of step (i) to an activated polyalkylene oxide in the presence of about 0.01 to about 2.0 M chloride anions so that a polyalkylene oxide conjugated hemoglobin having a p50 greater than that of normal human hemoglobin in whole red blood cells is obtained, when the p50 of said polyalkylene oxide conjugated hemoglobin and said normal human hemoglobin in whole red blood cells are measured under the same conditions. According to the method, the polyalkylene oxide comprises poly(ethylene glycol) and said activated polyalkylene oxide forms a urethane linkage with the ε-amino groups of the aforementioned hemoglobin.

U.S. Pat. No. 5,478,806 (Nho et al., 1995) titled "Enhancement of antitumor therapy with hemoglobin-based conjugates" disclosed a method of enhancing the effectiveness of antitumor therapy in mammals, comprising: administering to a mammal in need of such therapy an effective amount of radiation in combination with hemoglobin covalently conjugated to a poly(alkylene oxide), said hemoglobin conjugate being present in an amount sufficient to enhance the effectiveness of said radiation.

U.S. Pat. No. 6,844,317 (Winslow et al., 2005) titled "Methods for oxygen transport comprising a high oxygen affinity modified hemoglobin" disclosed a method of using a blood substitute product to deliver oxygen to a tissue, comprising administering to a mammal in need thereof a composition comprising: a) a blood substitute product adapted for delivery of oxygen to tissues comprising polyalkylene oxide (PAO) modified oxygenated hemoglobin, wherein the PAO modified oxygenated hemoglobin has a p50 less than native stroma-free hemoglobin from the same animal source when measured under the same conditions, and wherein the PAO modified oxygenated hemoglobin is stable towards autooxidation and has a methemoglobin/total hemoglobin ratio of less than 0.1; and b) an aqueous diluent.

U.S. Pat. No. 7,501,499 (Acharya et al., 2009) titled "Modified hemoglobin and methods of making same" disclosed a process for preparing a hemoglobin molecule (Hb) modified to have on average six±one polyethylene glycol (PEG) chains, comprising the steps of: (a) reacting Hb with 8-15 fold molar excess of iminothiolane to form thiolated Hb; and (b) reacting the thiolated Hb with 16-30 fold molar excess of PEG functionalized with a maleimide moiety, to form a modified Hb having on average six±one PEG chains.

U.S. Pat. No. 7,625,862 (Winslow et al., 2009) titled "Method for making a high oxygen affinity modified hemoglobin for oxygen transport" disclosed a method of making a blood substitute product comprising the steps of: a) preparing an oxygenated hemoglobin solution; b) thiolating the oxygenated hemoglobin to form thiolated oxygenated hemoglobin; and c) reacting the thiolated oxygenated hemoglobin with maleimidyl polyethylene glycol to form polyethylene glycol modified hemoglobin; wherein the polyethylene glycol modified hemoglobin has a p50 less than two thirds that of native stroma-free hemoglobin from the same animal source when measured under the same conditions.

U.S. Pat. No. 7,989,414 (Winslow et al., 2011) titled "Compositions for oxygen transport comprising a high oxygen affinity modified hemoglobin" disclosed a method of making a blood substitute product prepared by a process comprising the steps of: a) providing an oxygenated hemoglobin (Hb); b) combining the oxygenated Hb with a thiolating reagent to form thiolated oxygenated Hb; and c) reacting the thiolated oxygenated Hb with at least one thiol reactive polyalkylene oxide (PAO) having an alkyl linker to form a PAO surface-modified oxygenated Hb (PAO-Hb), wherein the PAO-Hb has a p50 less than two thirds that of native stroma-free hemoglobin from the same animal source when measured under the same conditions.

U.S. Pat. No. 8,021,858 (Vandegriff et al., 2011) titled "Method for making polyalkylene oxide modified hemoglobin" disclosed a method of making polyalkylene oxide (PAO) modified Hb useful for delivering oxygen to tissue, wherein a PAO-Hb conjugate having PAO moieties are covalently bound to cysteine, lysine, and histidine moieties on the surface of deoxygenated Hb.

U.S. Pat. No. 8,377,868 (Winslow et al., 2013) titled "Compositions for oxygen transport comprising a high oxygen affinity modified hemoglobin" disclosed a method of making polyalkylene oxide (PAO) polymer surface-modified oxygenated (PAO-Hb) having a p50 less than 15 torr as measured at a pH of 7.4 and a temperature of 37° C., prepared by a process comprising the steps of: thiolating an oxygenated hemoglobin to form thiolated oxygenated hemoglobin; and reacting the thiolated oxygenated hemoglobin with at least one polyalkylene oxide polymer to form the polyalkylene oxide surface-modified oxygenated hemoglobin (PAO-Hb), the polyalkylene oxide polymer comprising a thiol reactive moiety and polyalkylene oxide linked by a linker consisting of an alkylene or phenylene.

U.S. Pat. No. 8,609,815 (Vandegriff et al., 2013) titled "Methods for preparing stable deoxygenated PEG-hemoglobin conjugate solutions comprising an antioxidant" disclosed a method of making a polyethylene glycol hemoglobin (PEG-Hb) conjugate solution comprising the steps of: deoxygenating a PEG-Hb conjugate; and adding one or more antioxidants during or following the deoxygenating step to form the PEG-Hb conjugate solution; wherein PEG-Hb conjugate has a p50 less than 15 mmHg, and the PEG-Hb conjugate solution contains less than 10% methemoglobin after storage at 4° C., 25° C., or 40° C. for at least six months under deoxygenated conditions.

U.S. Pat. No. 9,241,979 (Winslow et al., 2016) titled "Compositions for oxygen transport comprising a high oxygen affinity modified hemoglobin" disclosed a method of making a modified hemoglobin having a p50 less than 15 torr as measured at 37° C. and pH 7.4, wherein the modified hemoglobin is hemoglobin, to which polyalkylene oxide has been covalently attached via a thiol reactive moiety to a thiol group of an amino acid side chain on the hemoglobin molecule while the hemoglobin is in the oxygenated state; the polyalkylene oxide being linked to the thiol reactive moiety by a linker consisting of alkylene or phenylene.

U.S. Pat. No. 10,029,001 (Vandegriff et al., 2018) titled "Diaspirin crosslinked pegylated hemoglobin" disclosed a method of making a β,β-intramolecularly-crosslinked polyalkylene oxide hemoglobin tetramer conjugate having a p50 ranging from about 2 to 5 mmHg as measured at 37° C. and pH 7.4, wherein the hemoglobin conjugate when fully deoxygenated at 25° C. exhibits a maximal nitrite reductase activity that is at least 10-fold greater than that of deoxygenated stroma-free hemoglobin when measured under the same conditions, wherein the hemoglobin is conjugated to on average about 7 to about 11 polyalkylene oxide molecules per tetramer.

U.S. Pat. No. 10,080,782 (Abuchowski et al., 2018) titled "Hemoglobin compositions" disclosed a method of making an aqueous pharmaceutical formulation capable of delivering oxygen or carbon monoxide (CO) to tissue of a subject to whom said formulation is administered, said formulation comprising a covalent conjugate between a functional, native hemoglobin molecule and at least one molecule of poly(ethylene glycol), and said formulation comprising: a. a water-soluble hemoglobin fraction comprising a group of bovine hemoglobin molecules wherein each member of said group of bovine hemoglobin molecules i. is bound to CO; ii. is covalently conjugated to at least one molecule of said poly(ethylene glycol) through an amine moiety of an amino acid residue; iii. is substantially free of chemical cross-linking agents; iv. includes less than 5% cross-linked hemoglobin; and iv. has a p50 of about 9 mm Hg to about 14 mm Hg; and b. a water-soluble stabilizer fraction rendering said group of bovine hemoglobin molecules oxidation resistant, said water-soluble stabilizer fraction comprising a stabilizing agent comprising a structural element more reactive with oxygen than said group of bovine hemoglobin molecules; and c. an aqueous diluent fraction comprising a pharmaceutically acceptable aqueous diluent in which said hemoglobin fraction is soluble, said formulation being essentially free of viral activity, and stably comprising less than about 10% methemoglobin after storage at 45° C. for at least about 4 days.

U.S. Pat. No. 10,172,950 (Abuchowski et al., 2019) titled "Hemoglobin compositions" disclosed a method of treating a condition that can be ameliorated by oxygenating the red blood cells of a patient in need of such treatment, by administering to said patient a therapeutically effective amount of a pharmaceutical formulation comprising a covalent conjugate between a functional, native hemoglobin (Hb) molecule and at least one molecule of poly(ethylene glycol) (PEG), said formulation comprising: a. a water-soluble hemoglobin fraction comprising a group of bovine hemoglobin molecules wherein each member of said group of bovine hemoglobin molecules: i. is bound to carbon monoxide (CO); ii. is covalently conjugated to at least one molecule of said poly(ethylene glycol) through an amine moiety of an amino acid residue; iii. is substantially free of chemical cross-linking agents; iv. includes less than 5% cross-linked hemoglobin; and v. has a p50 of about 7 mm Hg to about 16 mm Hg; and b. a water-soluble stabilizer fraction rendering said group of bovine hemoglobin molecules oxidation resistant, said water soluble stabilizer fraction comprising a stabilizing agent comprising a structural element more reactive with oxygen than said group of bovine hemoglobin molecules; and c. an aqueous diluent fraction comprising a pharmaceutically acceptable aqueous diluent in which said bovine hemoglobin fraction is soluble, said formulation being essentially free of viral activity, and stably comprising less than about 10% methemoglobin after storage at 45° C. for at least about 4 days.

U.S. Pat. No. 10,821,158 (Malavalli et al., 2020) titled "Polyalkylene oxide valerate hemoglobin conjugates" disclosed an invention related generally to polyethylene glycol (PEG) conjugated hemoglobins made by conjugation of succinimidyl-valerate activated polyethylene glycol to primary amines and N-terminal valines of the hemoglobin.

Donated human blood has limitations, such as strict storage requirements, short storage life, and the immune properties of red blood cells. In addition, supplements of human blood cannot keep up with demand for human blood, resulting in a lack of donated blood.

HBOCs have advantages over donated human blood, including diminished chance of disease transmission, no need to conduct blood typing, and longer storage life, and solve the aforementioned problems related to donated human blood. Therefore, there is a need in the art for novel type of HBOCs to act as a substitute for donated human blood.

The present inventors have found novel HBOCs that can serve as blood substitutes and have better therapeutic activity, and thus have devised the present invention.

DEFINITIONS

The definition of terms is provided below to facilitate understanding related to the invention.

The term "blood substitute" refers to a composition that can be used to replace blood received through blood transfusions in patients requiring oxygen and fluid replenishment, in medical conditions such as, blood-loss trauma, stroke, ischemia, surgery, anemia, or other blood loss-related injuries and diseases.

The term "hemoglobin" (Hb) refers to the protein residing within red blood cells that has the capability of carrying oxygen. Each molecule of hemoglobin has 4 subunits, two α subunits and two β subunits, which are clustered in a tetrameric structure. Each subunit contains one iron-containing heme group that binds oxygen. Each hemoglobin molecule can bind up to 4 oxygen molecules. Hemoglobin refers also to, with equal meaning, a native hemoglobin or an unmodified hemoglobin.

The term "crosslinked hemoglobin" (xHb) refers to a hemoglobin that is intra-molecularly crosslinked between subunits. Hb is a tetrameric protein consisting of 4 subunits, two α subunits and two β subunits. The crosslinking is made possible by reacting Hb with a crosslinking agent such as bis(3,5-dibromosalicyl) fumarate or bis(3,5-dibromosalicyl) succinate, resulting in xHb that can be crosslinked between any two subunits via the linkage of fumarate or succinate.

The term "native hemoglobin" refers to the hemoglobin that is purified from a red blood cell, with no modification done to it. The term is used in contrast to modified hemoglobin.

The term "hemoglobin-based oxygen carrier" (HBOC) refers to a group of modified hemoglobin compositions that use hemoglobin as an oxygen carrier for use as a blood substitute. HBOCs employ diverse technologies to render the hemoglobin biocompatible and less toxic to the body. The technologies include liposome encapsulation of hemoglobin, polymeric vesicle encapsulation of hemoglobin, intra-molecular (between subunits) cross-linking of hemoglobin, polymerization of hemoglobin, surface modification of hemoglobin such as PEGylation, and conjugation of hemoglobin with proteins, peptides, carbohydrates, and synthetic polymers.

The term "oxygen carrying capacity" refers to the capacity of a blood substitute to carry oxygen, but does not necessarily correlate to the efficiency of oxygen delivery. Oxygen carrying capacity is generally calculated based on hemoglobin concentration, with the known fact that 1 gram of hemoglobin can carry 1.34 ml of oxygen. Hemoglobin concentration can be measured by any method known in the art or by any applicable clinical instrument.

The term "polyethylene glycol" (PEG) refers to polymers of the general chemical formula $HO(CH_2CH_2O)_nH$, where n is an integer greater than 1. The group represented as $(CH_2CH_2O)_n$ is called the PEG backbone. The end group can be H or alkoxy of the general formula $CH_3(CH_2)_nO$, where n is 0 or any integer. The most common structure of PEG is linear, such as revealed in methoxy PEG or hydroxy PEG. However, the PEG can be of a diverse structure, including that of multi-armed PEG, branched PEG, or PEG with degradable linkages built within the backbone.

As used herein, "fatty acid" is aliphatic monocarboxylic acid derived from or contained in esterified form in an animal or vegetable fat, oil, or wax. Saturated fatty acid refers to a type of fatty acid in which all carbon-carbon bonds are single bonds, and unsaturated fatty acid refers to a type of fatty acid having double or triple bonds.

The term "FA-PEG" or "fatty acid-PEG" refers to fatty acid-linked PEG where one molecule of fatty acid is conjugated to one molecule of PEG. Specifically, it refers to fatty acid-linked PEG prepared by reacting a fatty acid derivative which is prepared from fatty acid with a PEG derivative, and more specifically, in which PEG and carbonyl of fatty acid are linked via specific linkages (e.g., linkages comprising amine or sulfur).

The term "PEGylate" or "PEGylation" refers to the art of conjugating PEG to the surface of a target protein, such as hemoglobin, wherein polyethylene glycol protects the target protein from loss of activity, and the composition can be injected into the mammalian circulatory system with substantially no immunogenic response.

The term "FA-PEGylate" or "FA-PEGylation" refers to the art of conjugating FA-PEG to the surface of the target protein, such as hemoglobin.

The term "alkoxy-PEG derivatives" or "functional alkoxy-PEG" refers to PEG having a particular functional group at the end of the PEG, with the functional group capable of reacting readily with an electrophile or a nucleophile on the target molecule, such as hemoglobin.

The term "FA-PEG derivatives" or "functional FA-PEG" refers to FA-PEG having a particular functional group at the end of the FA-PEG, with the functional group capable of reacting readily with an electrophile or a nucleophile on the target molecule, such as hemoglobin.

The term "FA-PEG-Hb" refers to FA-PEG-conjugated hemoglobin, wherein a molecule of hemoglobin is conjugated with one or more molecules of FA-PEG.

The term [FA-PEG]$_p$-Hb refers to Hb conjugated with FA-PEG, wherein p denotes the number of FA-PEGs conjugated to the Hb.

The term [FA-PEG]$_p$-Hb-[alkoxy-PEG]$_q$ refers to Hb conjugated with FA-PEG and alkoxy-PEG, wherein p denotes the number of FA-PEGs conjugated, and q denotes the number of alkoxy-PEGs conjugated to the Hb.

The term [FA-PEG]$_p$-xHb refers to xHb (crosslinked Hb) conjugated with FA-PEG, wherein p denotes the number of FA-PEGs conjugated to the xHb.

The term [FA-PEG]$_p$-xHb-[alkoxy-PEG]$_q$ refers to xHb conjugated with FA-PEG and alkoxy-PEG, wherein p denotes the number of FA-PEGs conjugated, and q denotes the number of alkoxy-PEGs conjugated to the xHb.

The term [Stearic-PEG]$_p$-Hb refers to Hb conjugated with stearic-PEG, wherein p denotes the number of stearic-PEGs conjugated to the Hb.

The term [Stearic-PEG]$_p$-Hb-[alkoxy-PEG]$_q$ refers to Hb conjugated with stearic-PEG and alkoxy-PEG, wherein p denotes the number of stearic-PEGs conjugated, and q denotes the number of alkoxy-PEGs conjugated to the Hb.

The term [Stearic-PEG]$_p$-xHb refers to xHb (crosslinked Hb) conjugated with stearic-PEG, wherein p denotes the number of stearic-PEGs conjugated to the xHb.

The term [Stearic-PEG]$_p$-xHb-[alkoxy-PEG]$_q$ refers to xHb (crosslinked Hb) conjugated with stearic-PEG and alkoxy-PEG, wherein p denotes the number of stearic-PEGs conjugated, and q denotes the number of alkoxy-PEGs conjugated to the xHb.

The term "half-life" or "$t_{1/2}$", as used herein in the context of administering a drug to a patient, is defined as the time required for plasma concentration of a drug in a patient to be reduced by one half.

The term "p50" refers to the oxygen tension when hemoglobin is 50% saturated with oxygen. When hemoglobin-oxygen affinity increases, the oxyhemoglobin dissociation curve shifts to the left and decreases p50. When hemoglobin-oxygen affinity decreases, the oxyhemoglobin dissociation curve shifts to the right and increases p50.

The expression "conjugation", "conjugating", or "conjugate" refers to the art of reacting target molecule, such as hemoglobin, with various reactant (e.g., FA-PEG derivative or alkoxy-PEG derivative) or the art of forming a covalent or direct linkage with desired parts of reactant (e.g., FA-PEG or alkoxy-PEG) by reaction with aforementioned reactant.

The term "alkyl" refers to a linear or branched, saturated hydrocarbon chain radical, including for example and in a non-limiting sense, ethyl, n-butyl, t-butyl, n-pentyl, octyl, dodecyl, octadecyl, etc.

The term "alkenyl" refers to a linear or branched, unsaturated hydrocarbon chain radical which includes one or more unsaturated bonds (e.g. double or triple bond), including for example and in a non-limiting sense, propenyl, butenyl, octenyl, dodecenyl, octadecenyl, etc.

The term "alkylene" refers to a divalent alkyl group, and the term "alkenylene" refers to a divalent alkenyl group.

The term "alkoxy" refers to an —O—R group, wherein R is alkyl, alkenyl, or substituted alkyl or alkenyl, etc. (e.g., methoxy or ethoxy).

The term "amide" refers to a divalent group which has the formula —N(R)CO—, wherein R is H, alkyl, alkenyl, aryl, arylalkyl, or the like.

The term "carbamate" and "urethane" refers to a divalent group which has the formula —OC(O)NR—, wherein R is H, alkyl, alkenyl, aryl, arylalkyl, or the like.

The term "carbonate" refers to a divalent group which has the formula —OC(O)O—.

The term "ester" refers to a divalent group which has the formula —OC(O)—.

The term "ether" refers a divalent group which has the formula —O—.

The term "carbonyl" refers to a divalent group which has the formula —C(O)—.

The term "ameliorating" or "ameliorate" refers to any indicia of success in the treatment of a pathology or condition, including any objective or subjective parameter, such as abatement, remission or diminishing of symptoms, or an improvement in a patient's physical or mental well-being. Amelioration of symptoms can be based on objective or subjective parameters, including the results of a physical examination and/or a psychiatric evaluation.

The term "deoxygenated" refers to hemoglobin in which the Fe(II) atom is bound to a species other than oxygen (e.g., carbon monoxide) or is not bound to oxygen or any other species.

As used herein, "pharmaceutically acceptable carrier" includes any material, which when combined with the conjugate retains the conjugate's activity and is non-reactive with the subject's immune system. Examples include, but are not limited to, any of the standard pharmaceutical carriers, such as a phosphate-buffered saline solution, water, emulsions such as oil/water emulsions, and various types of wetting agents. Other carriers may also include sterile solutions, tablets including coated tablets, and capsules. Typically such carriers contain excipients such as starch, milk, sugar, certain types of clay, gelatin, stearic acid or salts thereof, magnesium or calcium stearate, talc, vegetable fats or oils, gums, glycols, or other known excipients. Such carriers may also include flavor and color additives or other ingredients. Compositions comprising such carriers are formulated by well-known conventional methods. Exemplary carriers are hypertonic sodium chloride and isotonic sodium chloride (e.g., phosphate buffered saline). Hypertonic and isotonic carriers are useful in formulating deoxygenated PEGylated hemoglobin of the invention (e.g., carbon monoxide-bound iron, and unbound iron), in which the iron atom is bound to oxygen.

The term "treatment" or "treating" is to be understood as embracing prophylaxis and treatment or amelioration of symptoms of a disease and/or treatment of the cause of the disease. The term "prevention" or "preventing" is to be understood as all actions that inhibit or delay the development of a disease or disorder.

As used herein, terms such as "subject," "patient," and "mammal" are used interchangeably, and are exemplified by a human.

The term "aqueous solution" refers to a solution that contains some water and may also contain one or more other liquid substances with water to form a multi-component solution.

The meaning of other terminology used herein should be easily understood by any person skilled in the art.

SUMMARY OF THE INVENTION

The present invention provides a blood substitute product with oxygen carrying capability of modified hemoglobin. The hemoglobin derivative of the present invention exhibits non-toxicity, long-term stability, and extended intravascular retention time and provides a useful substitute for a blood and therapeutic agent for various diseases or disorders.

The present invention provides a hemoglobin derivative, in which hemoglobin (Hb) or crosslinked hemoglobin (xHb) is conjugated with fatty acid-PEG (FA-PEG) derivatives and alkoxy-PEG derivatives.

The present invention also provides a blood substitute composition comprising the hemoglobin derivative and a pharmaceutically acceptable carrier.

The present invention also provides a pharmaceutical composition, method, and use for treating, preventing, or alleviating a disease selected from the group consisting of hypoxia, ischemia, sepsis, sickle cell disease, retinal disease, diabetes, myocardial infarction, hemorrhagic shock, trauma, traumatic brain injury, brain stroke, tumor, and cancer.

The hemoglobin derivative of the present invention offers the technical effects related to toxicity and an increase in intravascular half-life and storage stability. In addition, the hemoglobin derivative has universal applicability as an oxygen carrier, such as a blood substitute as well as treatment of the various diseases or disorders.

Other aspects of the invention are described throughout the specification and other embodiments, and the objects and advantages of the invention are apparent based on the detailed description that follows.

DETAILED DESCRIPTION OF THE INVENTION

The present invention relates to a hemoglobin derivative in which hemoglobin (Hb) or crosslinked hemoglobin (xHb) is conjugated with fatty acid-PEG (FA-PEG) derivatives and alkoxy-PEG derivatives.

Hemoglobin can be isolated from red blood cells (RBC) of human blood, bovine blood, porcine blood, blood from any land or oceanic animal species, or recombinant, or from red blood cells produced by stem cell technology. The human blood can be collected from donor blood that has passed its shelf-life. The animal blood can be collected from live or freshly slaughtered donors. The blood should be collected in a sanitary manner.

The present invention may comprise crosslinked hemoglobin as well as native hemoglobin.

The crosslinked hemoglobin may be intramolecularly-crosslinked. More specifically, the crosslinked hemoglobin may be β,β-intramolecularly-crosslinked or α,α-intramolecularly-crosslinked by conventional methods known in the art.

The crosslinked hemoglobin may be produced by reacting hemoglobin with a crosslinking agent such as bis(3,5-dibromosalicyl) fumarate or bis(3,5-dibromosalicyl) succinate.

The crosslinking of hemoglobin may allow stabilization of the tetrameric structure of the hemoglobin with its subunits linked together by linkers and protection of hemoglobin from dissociating into non-functional subunits.

In the context of the present invention, the crosslinked hemoglobin may be applied to all embodiments of hemoglobin.

Polyethylene glycol when conjugated to hemoglobin may advantageously elicit pharmacokinetic changes such as diminished immunogenic reactions, increased intravascular retention time, and increased water solubility, and while maintaining oxygen delivery capability.

Fatty acid of the present invention may be effective in increasing the intravascular retention time of the fatty acid-linked PEG-conjugated hemoglobin (FA-PEG-Hb). This is made possible because fatty acids are known to readily bind with human serum albumin FA-PEG-Hb intravenously injected may come in contact with albumin that is abundantly present in human blood. FA-PEG-Hb bound with one or more molecules of albumin will possess larger molecular weight and larger molecular radius, which will in turn manifest increased intravascular half-life. As albumin is also known to have anti-oxidant activity, the presence of albumin bound to FA-PEG-Hb may deter the rate of naturally-occurring oxidation of hemoglobin.

The hemoglobin or crosslinked hemoglobin may be reduced or deoxygenated prior to the conjugation with FA-PEG derivatives and alkoxy-PEG derivatives.

In one embodiment, the fatty acid-PEG derivatives or alkoxy-PEG derivatives may be covalently conjugated to hemoglobin or crosslinked hemoglobin.

The hemoglobin or crosslinked hemoglobin may be conjugated via a biologically stable, nontoxic, covalent linkage to alkoxy-PEG or fatty acid-PEG. Such linkages may include, but are not limited to, urethane linkages, carbamate linkages, carbonate linkages, ester linkages, carbonyl linkages, succinimidyl linkages, secondary amine linkages or amide linkages. In one embodiment, the one side or both sides of terminal end-groups in an alkoxy-PEG derivative and an FA-PEG derivative may be modified to contain a reactive functional group, and specifically, electrophilic functional group to be readily conjugated with hemoglobin or crosslinked hemoglobin.

The fatty acid-PEG derivative and the alkoxy-PEG derivative may be conjugated with hemoglobin or crosslinked hemoglobin by reacting the reactive functional group of the fatty acid-PEG derivative and the alkoxy-PEG derivative with a functional group of hemoglobin or crosslinked hemoglobin.

A fatty-acid PEG derivative and an alkoxy-PEG derivative can be conjugated to the surface amino acid side chains such as cysteine residues, lysine residues, or the terminal valine residue of hemoglobin or crosslinked hemoglobin using known methods, specifically nucleophilic substitution reaction.

The reactive functional group of the derivatives serves to link fatty acid-PEG and alkoxy-PEG to hemoglobin or crosslinked hemoglobin, and is non-reactive in vivo after the linkage.

The fatty acid-PEG derivative may be prepared by nucleophilic substitution reaction. More specifically, the fatty acid-PEG may be formed by nucleophilic substitution reaction in which a fatty acid having an electrophilic functional group is attacked by a nucleophilic group of a PEG derivative (e g amine or thiol), resulting in the conjugation reaction between the fatty acid and the nucleophilic atoms of a PEG derivative (e.g. nitrogen of amine or sulfur of thiol), while the electrophilic functional group from a fatty acid is detached as a leaving group.

The fatty acid having an electrophilic functional group may be formed by substitution reaction of a carboxyl group of a fatty acid, resulting in substitution of a hydroxyl group of a carboxyl group with electrophilic functional group.

In the preferred embodiment, the alkoxy-PEG is a methoxy-PEG.

In one embodiment, the hemoglobin derivative may be represented by the following formula (I): [FA-PEG]$_p$-Hb-[alkoxy-PEG]$_q$, where p=1~10, and q=1~20; or the following formula (II): [FA-PEG]$_p$-xHb-[alkoxy-PEG]$_q$, where p=1~10, and q=1~20.

Formula (I) refers to the hemoglobin derivative in which hemoglobin (Hb) is conjugated with fatty acid-PEG (FA-PEG) derivatives and alkoxy-PEG derivatives, and formula (II) refers to the hemoglobin derivative in which crosslinked hemoglobin (xHb) is conjugated with fatty acid-PEG (FA-PEG) derivatives and alkoxy-PEG derivatives.

The mPEG-SS used in this Example is just one example of many PEG derivatives with varying molecular weight that can be used. Many other PEG derivatives that are reactive towards the amine on the surface of Hb can be used.

In one embodiment, the FA-PEG derivatives may be, but not limited to, any derivatives which comprise fatty acid-PEG and can be readily reacted with hemoglobin or crosslinked hemoglobin to be conjugated therewith. The FA-PEG derivatives may be selected from the group consisting of FA-PEG acetaldehyde, FA-PEG propionaldehyde, FA-PEG butyraldehyde, FA-PEG maleimide, FA-PEG succinimidyl carbonate, FA-PEG succinimidyl carboxymethyl, FA-PEG succinimidyl glutarate, FA-PEG succinimidyl propionate, FA-PEG succinimidyl succinate, and FA-PEG succinimidyl carboxymethyl ester. More preferably, the FA-PEG derivatives may be FA-PEG succinimidyl carboxymethyl ester. The structural forms of the FA-PEG can be also diverse, and the examples include, but are not limited to, linear FA-PEG, branched FA-PEG, or FA-PEG with degradable linkages built within the backbone.

In one embodiment, the alkoxy-PEG derivatives may be, but are not limited to, any derivatives which comprise alkoxy-PEG and can be readily reacted with hemoglobin or crosslinked hemoglobin to be conjugated therewith. The alkoxy-PEG derivatives may be selected from the group consisting of alkoxy-PEG acetaldehyde, alkoxy-PEG propionaldehyde, alkoxy-PEG butyraldehyde, alkoxy-PEG maleimide, alkoxy-PEG succinimidyl carbonate, alkoxy-PEG succinimidyl carboxymethyl, alkoxy-PEG succinimidyl glutarate, alkoxy-PEG succinimidyl propionate, and alkoxy-PEG succinimidyl succinate. More preferably, the alkoxy-PEG derivatives may be alkoxy-PEG succinimidyl succinate, and most preferably, the alkoxy-PEG derivatives may be methoxy-PEG succinimidyl succinate. The structural forms of the alkoxy-PEG can be also diverse, and the examples include, but are not limited to, linear alkoxy-PEG, branched alkoxy-PEG, or alkoxy-PEG with degradable linkages built within the backbone.

In one embodiment, the fatty acid may be saturated fatty acid or unsaturated fatty acid.

The saturated fatty acid or the unsaturated fatty acid may have the number of carbons from 6 to 24, preferably from 10 to 24.

The saturated fatty acids can be such as, but are not limited to, stearic acid, palmitic acid, myristic acid, lauric acid, capric acid, or arachidic acid. The unsaturated fatty acids can be such as, but are not limited to, oleic acid, linoleic acid, myristoleic acid, palmitoleic acid, or arachidonic acid.

The fatty acid which is used to form the fatty acid-PEG derivatives may have a molecular weight of about 60~400 Da, preferably 80~340 Da.

In one embodiment, the PEG has molecular weight of about 100~100,000 Da. Exemplary molecular weights of PEG include about to about 1,000~100,000 Da; about 1,000 to about 80,000 Da; about 1,000 to about 70,000 Da; preferably, about 1,000 to about 50,000 Da; and more preferably, about 2,000 to about 10,000 Da.

In a specific embodiment, the hemoglobin derivative is represented by the following formula (III) or following formula (IV):

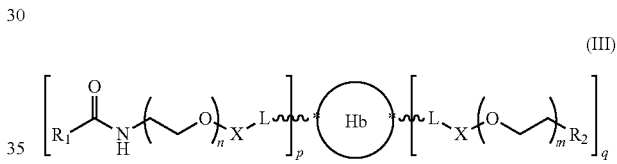

(III)

where p=1~10, q=1~20, n and m=each independently 20~2,000, $R_1$ is $C_{6-24}$ alkyl or $C_{6-24}$ alkenyl, $R_2$ is $C_{1-6}$ alkoxy, L is each independently NH or S, and X is each independently a divalent linker group with at least one amide, carbamate, carbonate, ester, ether, carbonyl, urethane, or succinimidyl;

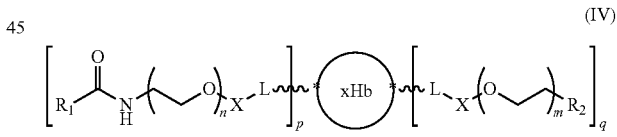

(IV)

where p=1~10, q=1~20, n and m=each independently 20~2,000, $R_1$ is $C_{6-24}$ alkyl or $C_{6-24}$ alkenyl, $R_2$ is $C_{1-6}$ alkoxy, L is each independently NH or S, and X is each independently a divalent linker group with at least one amide, carbamate, carbonate, ester, ether, carbonyl, urethane, or succinimidyl.

Formula (III) refers to the hemoglobin derivative in which hemoglobin (Hb) is conjugated with fatty acid-PEG (FA-PEG) derivatives and alkoxy-PEG derivatives, and formula (IV) refers to the hemoglobin derivative in which crosslinked hemoglobin (xHb) is conjugated with fatty acid-PEG (FA-PEG) derivatives and alkoxy-PEG derivatives.

In one embodiment, PEG of fatty acid-PEG and alkoxy-PEG may be covalently attached via an amino reactive moiety or sulfur reactive moiety of an amino acid side chain on the hemoglobin or crosslinked hemoglobin. The amino reactive moiety or sulfur reactive moiety may be linked to the PEG by group X. That is, X refers to the divalent linker group which links alkoxy-PEG and hemoglobin or crosslinked hemoglobin, or links fatty acid-PEG and hemoglobin or crosslinked hemoglobin.

In a specific embodiment, X is selected from the group consisting of amide, carbamate, carbonate, ester, ether, carbonyl, urethane, succinimidyl, $C_{1-6}$ alkylene, $C_{1-6}$ alkylene-amide, $C_{1-6}$ alkylene-carbamate, $C_{1-6}$ alkylene-carbonate, $C_{1-6}$ alkylene-ester, $C_{1-6}$ alkylene-ether, $C_{1-6}$ alkylene-carbonyl, $C_{1-6}$ alkylene-urethane, $C_{1-6}$ alkylene-succinimidyl, amide-$C_{1-6}$ alkylene-carbonyl, carbamate-$C_{1-6}$ alkylene-carbonyl, carbonate-$C_{1-6}$ alkylene-carbonyl, ester-$C_{1-6}$ alkylene-carbonyl, ether-$C_{1-6}$ alkylene-carbonyl, carbonyl-$C_{1-6}$ alkylene-carbonyl, urethane-$C_{1-6}$ alkylene-carbonyl, and succinimidyl-$C_{1-6}$ alkylene-carbonyl.

More preferably, X of FA-PEG derivatives may be amide-$C_{1-6}$ alkylene-carbonyl and X of alkoxy-PEG derivatives may be carbonyl-$C_{1-6}$ alkylene-carbonyl.

X may be derived from the FA-PEG derivatives and alkoxy-PEG derivatives, and L may be derived from the hemoglobin or crosslinked hemoglobin.

In one embodiment, linkage between L and X may be formed by a nucleophilic substitution reaction in which an FA-PEG derivative or an alkoxy-PEG derivative having an electrophilic functional group is attacked by the nucleophilic groups of hemoglobin or crosslinked hemoglobin (e g amines or thiols), resulting in the conjugation reaction between the FA-PEG derivative or alkoxy-PEG derivative and the nucleophilic atoms of hemoglobin (e.g. nitrogen of amines or sulfur of thiols), while the functional group from an FA-PEG derivative or an alkoxy-PEG derivative is detached as a leaving group.

In one embodiment, in the case that L is S, X is succinimidyl or $C_{1-6}$ alkylene-succinimidyl.

In the formula (III), p denotes the number of FA-PEGs conjugated to hemoglobin, and q denotes the number of alkoxy-PEGs conjugated to hemoglobin.

In the formula (IV), p denotes the number of FA-PEGs conjugated to crosslinked hemoglobin, and q denotes the number of alkoxy-PEGs conjugated to crosslinked hemoglobin.

The number p is preferably 1 to 8, more preferably, 1 to 6, and most preferably, 1 to 4. The number q is preferably 2 to 18, more preferably, 4 to 16, and most preferably, 10 to 16.

In the formulas (III) and (IV), n and m are each independently the average number of oxyethylene units of a PEG, and preferably, n and m are each independently 20 to 1,800, more preferably, 50 to 1,800, and most preferably, 100 to 1,500.

$R_1$ corresponds to a hydrocarbon chain which is comprised in a fatty acid. In one embodiment, $R_1$ is $C_{6-24}$ alkyl or $C_{6-24}$ alkenyl, preferably, $R_1$ is $C_{10-24}$ alkyl or $C_{10-24}$ alkenyl, and more preferably, $R_1$ is $C_{10-22}$ alkyl or $C_{10-22}$ alkenyl. In one embodiment, in the case that $R_1$ is $C_{6-24}$ alkenyl, $R_1$ may have 1 to 5 unsaturated bonds.

In one embodiment, $R_2$ is alkoxy, preferably, $R_2$ is alkoxy, and most preferably, $R_2$ is methoxy.

The present invention further relates to the method for preparing the hemoglobin derivative, comprising reacting hemoglobin (Hb) or crosslinked hemoglobin (xHb) with the FA-PEG derivatives and the alkoxy-PEG derivatives to provide hemoglobin derivative conjugated with FA-PEG derivatives and alkoxy-PEG derivatives.

In one embodiment, reaction of FA-PEG derivatives and reaction of alkoxy-PEG derivatives may be progressed simultaneously or progressed in turns.

In one specific embodiment, hemoglobin derivative may be prepared by reaction of hemoglobin or crosslinked hemoglobin with both FA-PEG derivatives and alkoxy-PEG derivatives simultaneously in one single step.

In other specific embodiment, hemoglobin derivative may be prepared by reaction of hemoglobin or crosslinked hemoglobin first with FA-PEG derivatives, followed by reaction with alkoxy-PEG derivatives, or may be prepared by reaction of hemoglobin or crosslinked hemoglobin first with alkoxy-PEG derivatives, followed by reaction with FA-PEG derivatives.

In the case of the method for preparing the hemoglobin derivative from crosslinked hemoglobin, firstly, crosslinked hemoglobin may be prepared by reacting hemoglobin with a crosslinking agent such as bis(3,5-dibromosalicyl) fumarate or bis(3,5-dibromosalicyl) succinate prior to undergoing a reaction with FA-PEG derivatives and alkoxy-PEG derivatives.

In one embodiment, the reaction is performed in a buffer solution at the temperature of 4 to 35° C. and pH of 6 to 9.

In a specific embodiment, the reaction may be performed in a buffer solution at a temperature of 4° C. to 35° C., preferably at a temperature of 10° C. to 30° C., and most preferably at a temperature of 15° C. to 28° C.

In an additional specific embodiment, the reaction may be performed in a buffer solution at a pH of 6 to 9, preferably at a pH of 6.5 to 9, preferably at a pH of 7 to 9, preferably at a pH of 7 to 8.5, and preferably at a pH of 7.5 to 8.5.

The reaction of FA-PEG derivatives and the reaction of alkoxy-PEG derivatives respectively may be performed under different conditions or may be performed in the same conditions.

After the reaction, the product may be diafiltered (e.g. using a diafiltration membrane device) and/or passed through chromatography (e.g. ion-exchange chromatography, affinity chromatography or size exclusion chromatography) to separate the desired product from a reactant, such as unreacted hemoglobin, unreacted FA-PEG derivatives, and unreacted alkoxy-PEG derivatives, and to only collect the desired product.

The present invention further relates to a blood substitute composition comprising the hemoglobin derivative.

The hemoglobin derivative can be used as a blood substitute in that they are hemoglobin-based and are capable of delivering carbon monoxide as well as oxygen to tissues in a subject.

The present invention further relates to a pharmaceutical composition comprising the hemoglobin derivative for treating, preventing, or alleviating a disease selected from the group consisting of hypoxia, ischemia, sepsis, sickle cell disease, retinal disease, diabetes, myocardial infarction, hemorrhagic shock, trauma, traumatic brain injury, brain stroke, tumor, and cancer.

The blood substitute composition and the pharmaceutical composition can comprise a pharmaceutically acceptable carrier as well as the hemoglobin derivative.

Examples of a pharmaceutically acceptable carrier comprise any diluent, such as a protein, a glycoprotein, a polysaccharide, and other colloids, any salt that is pharmaceutically acceptable for delivery to a mammal, such as KCl, NaCl, $NaHCO_3$, $NaH_2PO_4.2H_2O$, $MgSO_4.2H_2O$, $CaCl_2.2H_2O$, cysteine, and dextrose.

The compositions of the invention may be isotonic, hypertonic, or hypotonic. In various embodiments, the composition is isotonic. In an exemplary embodiment, the composition includes a sufficient amount of salts to render it isotonic. In other embodiments, the diluent is isotonic phosphate buffered saline.

The composition can additionally comprise pharmaceutically-acceptable fillers and other materials well-known in the art, the selection of which depends on the dosage form, the condition being treated, the particular purpose to be achieved according to the determination of the ordinarily skilled artisan in the field and the properties of such additives. For example, the composition can include a physiological buffer, a carbohydrate (e.g. glucose, mannitol, or sorbitol), alcohol or poly alcohol, a pharmaceutically acceptable salt (e.g., sodium or potassium chloride), a surfactant (e.g., polysorbate 80), an anti-oxidant, an anti-bacterial agent, an oncotic pressure agent (e.g. albumin or polyethylene glycol), or a stabilizer (e.g., ascorbic acid, glutathione, or N-acetyl cysteine).

In a preferred embodiment, the composition may include stabilizers such as, but not limited to cysteine, N-acetyl cysteine, glutathione, or ascorbate.

In a preferred embodiment, the pharmaceutical composition may be formulated in an aqueous saline solution, specifically, an aqueous isotonic saline solution, and more specifically, a physiologically acceptable electrolyte-containing aqueous isotonic saline solution.

A composition of the present invention can be administered by injecting the composition directly and/or indirectly into the circulatory system of the subject by one or more injection methods.

Examples of direct injection methods may include intravascular injections, such as intravenous and intra-arterial injections, and intracardiac injections. Examples of indirect injection methods include intraperitoneal injections, subcutaneous injections, such that the hemoglobin derivative will be transported by the lymph system into the circulatory system, or injections into the bone marrow by means of a trocar or catheter. The compositions can also be administered by gavage. A preferred injection method may be an intravascular injection.

In one embodiment, the composition is administered simultaneously, separately, or sequentially in combination with one or more additional therapeutic agents to a subject in need thereof.

The present invention also relates to a method of treating, preventing, or alleviating a disease selected from the group consisting of hypoxia, ischemia, sepsis, sickle cell disease, retinal disease, diabetes, myocardial infarction, hemorrhagic shock, trauma, traumatic brain injury, brain stroke, tumor, and cancer, comprising administering the hemoglobin derivative to a subject in need thereof.

The hemoglobin derivative can be used as a therapeutic agent for various types of tumors and cancers. More effectively, the hemoglobin derivative can be used to oxygenate the solid tumors and cancers that are known to be hypoxic and thus resistant to chemotherapy and radiotherapy. Oxygenation of hypoxic tumor or cancer cells is known to render such cells more susceptible to therapy.

Generally an effective administration amount of a hemoglobin derivative of the invention will depend on the relative efficacy of the hemoglobin derivative chosen, the severity of the disorder being treated and/or prevented, and the weight of the subject.

The present invention also relates to use of the hemoglobin derivative as a medicament.

The present invention relates to use of the hemoglobin derivative for treating, preventing, or alleviating a disease selected from the group consisting of hypoxia, ischemia, sepsis, sickle cell disease, retinal disease, diabetes, myocardial infarction, hemorrhagic shock, trauma, traumatic brain injury, brain stroke, tumor, and cancer.

The hemoglobin derivative and compositions of the present invention can be used during various surgical procedures. For example, they can be used as an adjunct to angioplasty, thoracic aortic repairs, during a cardiopulmonary bypass procedure, or as a cardiopulmonary priming solution.

The present invention is additionally explained below by means of examples. These explanations must by no means be interpreted as a limitation to the scope of the invention as defined in the claims.

EXAMPLES

Example 1: Preparation of Native Pure Hemoglobin

Hemoglobin can be isolated from red blood cells (RBC) of human blood, bovine blood, porcine blood, or blood from other animal species. The human blood can be collected from donated blood that has passed its shelf-life. The animal blood can be collected from live or freshly slaughtered donors. The blood should be collected in a sanitary manner.

The methods are those known in the art for the process of isolation and purification of hemoglobin from blood, and these methods were generally applicable to the compositions of the present invention. The description following herein is illustrative and not limiting.

At the time of blood collection, the blood was mixed with an anticoagulant to prevent blood coagulation. Blood anticoagulants are well known in the art and include, for example, sodium citrate, ethylenediamine tetra-acetic acid, and heparin.

The collected blood was centrifuged to separate plasma-borne proteins from red blood cells (RBC). The RBCs were obtained as a precipitate in the centrifuge tube by draining the top fluid.

The collected RBCs were then mixed with isotonic saline, and subsequently washed with isotonic saline by a suitable means, such as by diafiltration, to separate RBCs from residual blood-borne plasma proteins, such as serum albumins or antibodies. The diafiltration was continued until several volumes of filtrate solution were consumed to achieve 99% removal of plasma proteins. In general, the diafiltration of RBCs utilizing 6 volumes of isotonic solution may remove about 99% of plasma protein and antibodies.

After the washing of RBCs, the Hb was extracted from the RBCs. Extraction can be performed by various methods including lysis and hypo-osmotic swelling and compression of the RBCs. Various RBC lysis methods exist, such as mechanical lysis, chemical lysis, and hypotonic lysis.

Following the lysis, the lysed RBC solution was then ultrafiltered to remove debris, such as red cell membrane particles. An appropriate ultrafiltration device is one that can separate native hemoglobin from large cell debris, and such a device may have molecular weight cut-off of 100,000 Da so that native hemoglobin having molecular weight of 65,000 Da can be separated from large particles. Other methods for separating Hb from the lysed cell debris can be used, including centrifugation, sedimentation, and microfiltration, or a combination of two or more methods.

The collected Hb solution was concentrated to be suitable for the next step by using an ultrafiltration device having molecular weight cut-off of 30,000 Da or lower in order to retain and collect the Hb in a solution while squeezing the excess water out.

The concentrated Hb solution was directed into an ion-exchange chromatography to purify the Hb by removing residual contaminants such as plasma proteins, antigens, antibodies, endotoxins, membrane lipids, and phospholipids. Further purification can be achieved by additional chromatography employing size exclusion, ion-exchange, or hydrophobic-interaction chromatography, or sequential combination of two or more types of chromatography.

The purified Hb solution was then treated with reduction methods to prevent Hb from oxidation. The native Hb without the protection of the RBC membrane tends to oxidize such that the ferrous iron ($Fe^{++}$) residing inside the heme pocket of Hb was liable to oxidize to become ferric iron ($Fe^{+++}$). The Hb with ferric iron was called Met-Hb. Ferric iron does not bind with oxygen, and thus the Met-Hb loses its oxygen carrying capability.

The stabilization of Hb can be achieved by deoxygenation or by addition of chemical reductants, or both. The Hb exposed to atmosphere is readily oxygenated to oxy-Hb which becomes liable for oxidation to Met-Hb. To deoxygenate, the oxy-Hb was directed through courses of a gas exchange device utilizing extra-luminal pressure of inert gases such as nitrogen, argon, or helium. Nitrogen is often the most safe and inexpensive choice. Deoxygenation of oxy-Hb can also be aided by addition of reductants such as, but not limited to, cysteine, N-acetyl-L-cysteine (NAC), glutathione, dithionate, or ascorbate.

The deoxygenated Hb solution was then directed to a condition of a thermal viral deactivation process. The thermal viral deactivation process relates to exposing the solution to a temperature that was raised sufficiently and for a time sufficient to deactivate essentially all viral activity in said solution. The thermal viral deactivation process is well known in the art, and it often employs the condition of raising the temperature of said solution to 60° C. and sustaining the temperature for 4 hours or more. An alternative to the thermal viral deactivation process is using a virus filtration device, and having the said solution pass through a virus filtration device. After the virus deactivation, the purified Hb solution is refrigerated or frozen for storage purposes.

Example 2: Preparation of a Stearic-PEG Derivative

In this exemplary embodiment, stearic acid is selected as a representative example of a saturated fatty acid.

In this exemplary embodiment, as an example of an FA-PEG derivative, stearic-PEG-succinimidyl carboxymethyl ester was prepared.

In the first step of synthesis, stearic acid in an organic solvent of methylene chloride was reacted with 1-ethyl-3-(3-dimethylaminopropyl)carbodiimide (EDC) and N-hydroxy succinimide (NHS) to obtain succinimidyl stearate. The reaction mechanism is illustrated below.

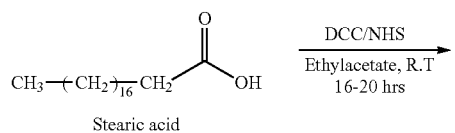

Stearic acid

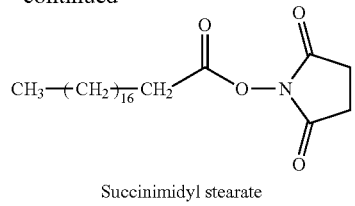

Succinimidyl stearate

In the second step of synthesis, PEG (PEG-diol) was first reacted in organic solvent of methylene chloride (MC) and triethylamine and tosyl chloride with a subsequent addition of 28% ammonia water. In the exemplary embodiment, PEG with a molecular weight of 5,000 Da is used. The intermediate PEG compounds thus formed were a mixture of HO-PEG-OH (PEG-diol), amine-PEG-OH (amine PEG-alcohol), and amine-PEG-amine (PEG-diamine), shown as compounds (1) in the illustration below. This mixture was then directed to pass through an ion-exchange chromatography to separate and to only obtain amine-PEG-OH, shown as compound (2) of the illustration below. The amine-PEG-OH was then reacted in organic solvent of MC with triethylamine and di-tert-butyl dicarbonate ($BOC_2O$) to obtain BOC-PEG-OH, shown as compound (3) in the illustration below. The BOC-PEG-OH was then reacted with ethylisocyanoacetate ($OCNCH_2CO_2$-ethyl) and triethanolamine (TEA) with the addition of 1N NaOH to obtain BOC-PEG-urethane acetic acid, which was then directed to pass through an ion-exchange chromatography to obtain further purified BOC-PEG-urethane acetic acid, shown as compound 4 in the illustration below. The BOC-PEG-urethane acetic acid was reacted with trifluoroacetic acid ($CF_3COOH$) to remove the BOC group and finally to obtain the amine-PEG-urethane acetic acid, shown as compound (5) in the illustration below.

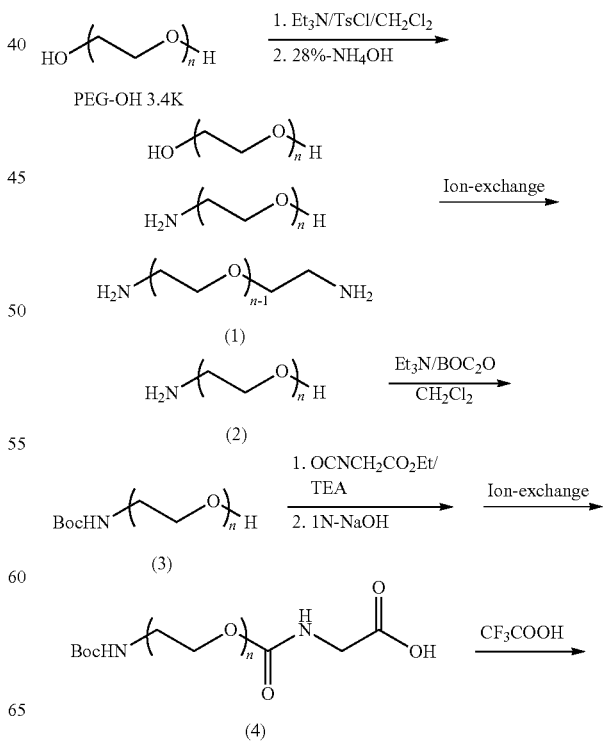

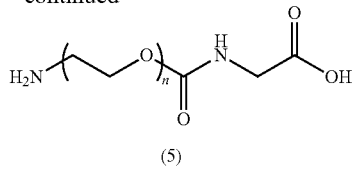

(5)

In the third step of synthesis, the succinimidyl stearate (from the first step) was reacted with amine-PEG-urethane acetic acid (from the second step) in the organic solvent of methylene chloride (MC) with the addition of base N,N-diisopropylethylamine (DIEA) under a room temperature (RT) for 16 hours to obtain the stearic-PEG-acid, as illustrated below. This compound has an acid end group, which is derivatized in the next step.

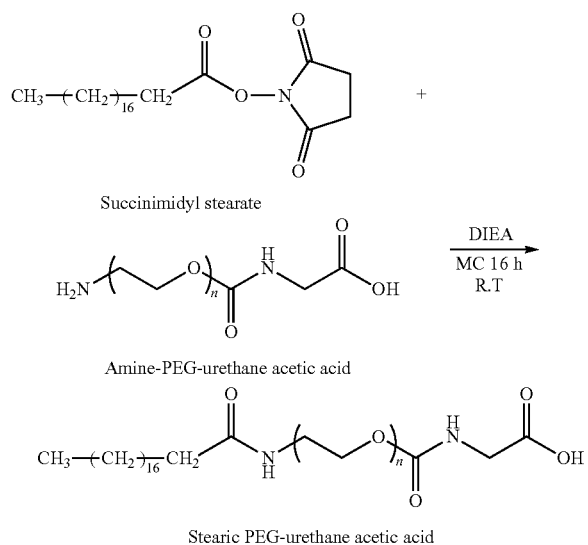

In the fourth step of synthesis, the stearic-PEG-acid obtained above was reacted in the organic solvent of MC along with N-hydroxy succinimide (NHS) and N,N-dicyclohexylcarbodiimide (DCC) under RT for 16~20 hours to obtain stearic-PEG-urethane-succinimidyl carboxymethyl ester as illustrated below. This stearic-PEG-urethane-succinimidyl carboxymethyl ester (Stearic-PEG-SCM) will be used to conjugate with Hb in Example 3.

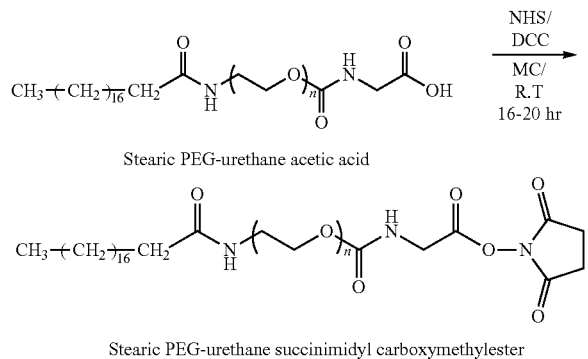

Example 3: Preparation of [Stearic-PEG]$_p$-Hb-[mPEG]$_q$

[Stearic-PEG]$_p$-Hb-[mPEG]$_q$ is a Hb conjugated with both stearic-PEG and mPEG.

The pure Hb obtained from Example 1 was first reacted with stearic-PEG-urethane succinimidyl carboxymethyl ester of MW 5,000 Da (Stearic-PEG-SCM) obtained from Example 2 to yield [Stearic-PEG]$_p$-Hb in the following process.

The Hb solution was prepared in an isotonic buffer solution at 22° C. at pH 8.2 with Hb concentration at 5% (w/v). Into the Hb solution was added 5 molar equivalents of stearic-PEG-SCM and well agitated for 2 hours. As a result, [Stearic-PEG]$_p$-Hb was obtained. The schematics of the reaction is illustrated below.

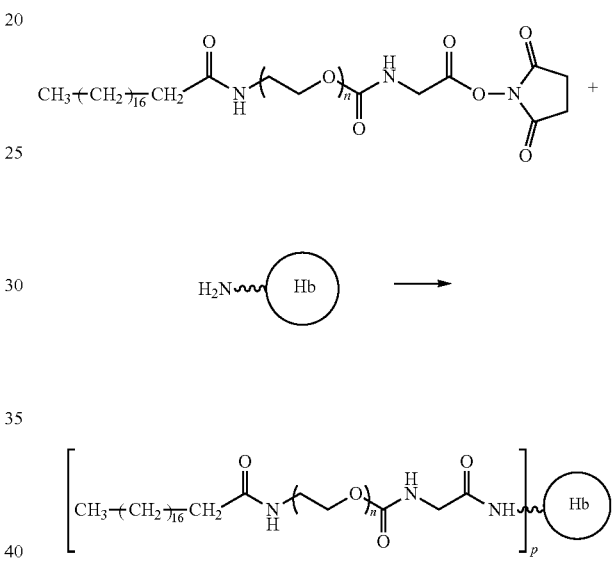

After the conjugation reaction, [Stearic-PEG]$_p$-Hb was diafiltered against diluent of an isotonic buffer to remove unreacted Hb and unreacted stearic-PEG. The diafiltration may use a diafiltration membrane device having molecular weight cut-off of 50,000 Da to separate the [Stearic-PEG]$_p$-Hb from unreacted Hb and unreacted stearic-PEG.

After the diafiltration, the [Stearic-PEG]$_p$-Hb solution was further directed to pass through an ion-exchange chromatography to separate out and eliminate the undesired portion of the [Stearic-PEG]$_p$-Hb and to only collect the desired portion of the [Stearic-PEG]$_p$-Hb. The conjugate was a mixture of different molecular weights including [Stearic-PEG]$_1$-Hb, [Stearic-PEG]$_2$-Hb, [Stearic-PEG]$_3$-Hb, and so on. Using proper chromatography, one may separate and obtain a desired portion.

The purified [Stearic-PEG]$_p$-Hb was then reacted with methoxy PEG-succinimidyl succinate of MW 5,000 Da (mPEG-SS). The [Stearic-PEG]$_p$-Hb was prepared in isotonic buffer at pH 8.2 and at 22° C. with a Hb concentration of 5% (w/v). Into the [Stearic-PEG]$_p$-Hb solution was added an amount of mPEG-SS at 15 molar equivalents and well agitated for 2 hours. As a result, [Stearic-PEG]$_p$-Hb-[mPEG]$_q$ was obtained. The schematics of the reaction is illustrated below.

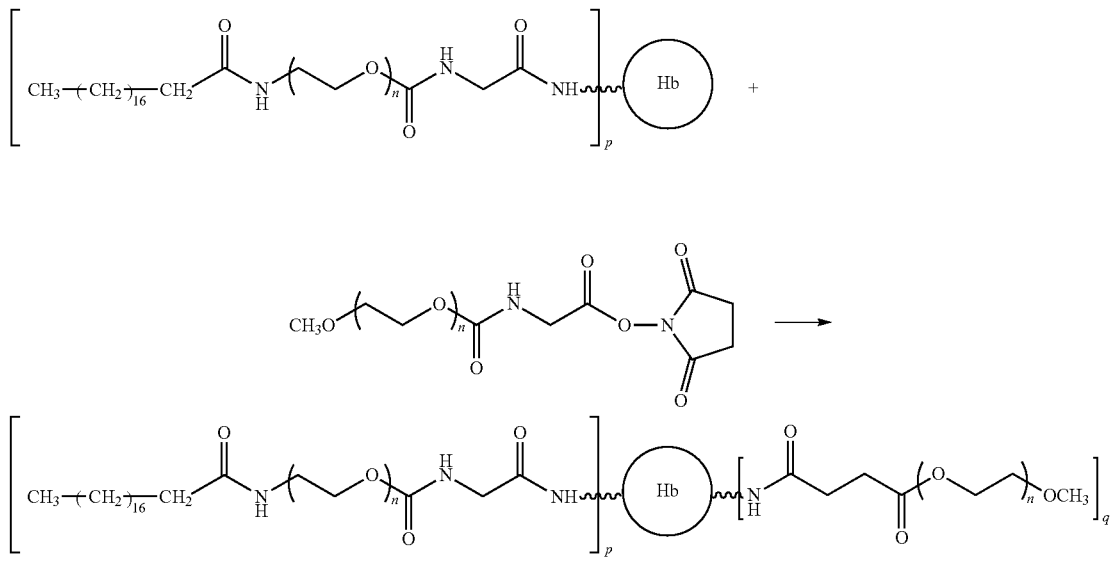

After pegylation with mPEG-SS, the resulting compound, [Stearic-PEG]$_p$-Hb-[mPEG]$_q$, was directed through diafiltration followed by chromatography in order to remove unreacted mPEG-SS and obtain a portion of the final compound with a desired molecular weight. The final compound may be formulated into a physiologically acceptable electrolyte-containing aqueous isotonic saline solution, and optionally stabilizers such as, but not limited to, cysteine, N-acetyl cysteine, glutathione, or ascorbate, can be added.

In this example, [Stearic-PEG]$_p$-Hb-[mPEG]$_q$ was prepared by pegylation of Hb first with an FA-PEG derivative, followed by pegylation with a mPEG derivative. However, the sequence of pegylation may be reversed in that [Stearic-PEG]$_p$-Hb-[mPEG]$_q$ may be prepared by pegylation of Hb first with a mPEG derivative, followed by pegylation with an FA-PEG derivative, to achieve an identical result.

Example 4: Preparation of [Stearic-PEG]$_p$-xHb-[mPEG]$_q$

[Stearic-PEG]$_p$-xHb-[mPEG]$_q$ is a xHb (crosslinked Hb) pegylated with both stearic-PEG and mPEG. First, Hb is crosslinked to make xHb (crosslinked Hb). This xHb is next conjugated with stearic-PEG-SCM and mPEG-SS.

The xHb was prepared by reacting Hb with bis(3,5-dibromosalicyl) fumarate. A Hb solution was prepared at 5% (w/v) concentration, a pH of 8.2, and a temperature of 22° C. in an isotonic buffer. The amount of bis(3,5-dibromosalicyl) fumarate added was 2 molar equivalents with respect to Hb. The reaction solution was well agitated for 2 hours to obtain the xHb solution. The schematics of the reaction is illustrated below.

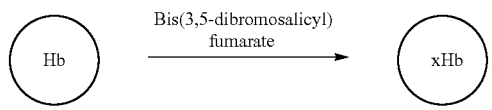

Next, xHb was prepared in an aqueous solution containing isotonic buffers at 22° C. with a pH of 8.2 and a Hb concentration at 5% (w/v). Into the xHb solution, 5 molar equivalents of stearic-PEG-SCM was added, which was well agitated for 2 hours to obtain [Stearic-PEG]$_p$-xHb. The schematics of the reaction is illustrated below.

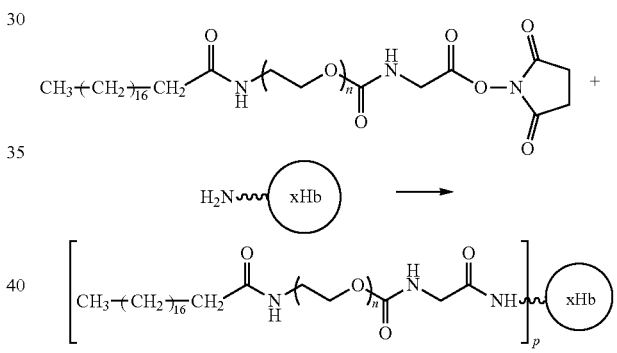

After the conjugation, the [Stearic-PEG]$_p$-xHb solution was diafiltered against diluent of an isotonic buffer to remove unreacted Hb and unreacted stearic-PEG. Such diafiltration may use a diafiltration membrane device with molecular weight cut-off of 50,000 Da. The 50,000 Da diafiltration membrane device may be effective in terms of separating the [Stearic-PEG]$_p$ from unreacted stearic-PEG.

After the diafiltration, the [Stearic-PEG]$_p$-xHb solution was further directed to pass through ion-exchange chromatography to separate out and eliminate the undesired portion of the [Stearic-PEG]$_p$-xHb, and to only collect the desired portion of the [Stearic-PEG]$_p$-xHb. The conjugate was a mixture of different molecular weights, including [Stearic-PEG]$_{1-x}$Hb, [Stearic-PEG]$_2$-xHb, [Stearic-PEG]$_3$-xHb, and so on. Using appropriate chromatography, one may separate and obtain the desired portion.

Next, [Stearic-PEG]$_p$-xHb was prepared in an aqueous solution containing isotonic buffers at 22° C. along with a pH of 8.2 and a Hb concentration of 5% (w/v). Into the [Stearic-PEG]$_p$-xHb solution, 15 molar equivalents of mPEG-SS was added, which was well agitated for 2 hours, to obtain [Stearic-PEG]$_p$-xHb-[mPEG]$_q$. The schematics of the reaction is illustrated below.

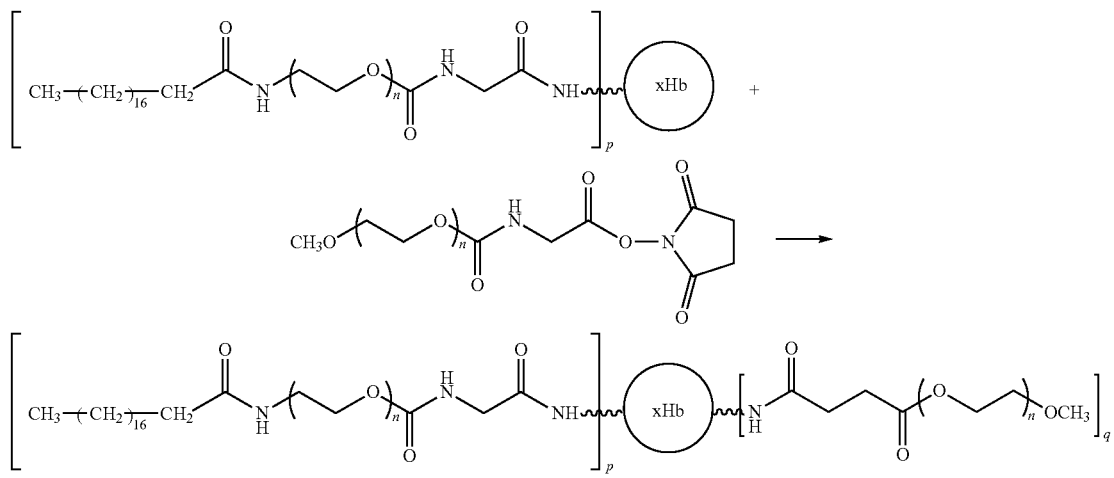

After the reaction with mPEG-SS, the resulting compound, [Stearic-PEG]$_p$-xHb-[mPEG]$_q$, was directed through diafiltration followed by chromatography in order to remove unreacted mPEG-SS to obtain desired a portion of the final compound with a desired molecular weight. The final compound may be formulated into a physiologically acceptable electrolyte-containing aqueous isotonic saline solution, along with optionally adding stabilizers.

In this example, [Stearic-PEG]$_p$-xHb-[mPEG]$_q$ was prepared by pegylation of xHb first with a FA-PEG derivative, followed by pegylation with an mPEG derivative. However, the sequence of pegylation may be reversed in that [Stearic-PEG]$_p$-xHb-[mPEG]$_q$ may be prepared by pegylation of xHb first with an mPEG derivative, followed by pegylation with a FA-PEG derivative, to achieve an identical result.

Example 5: Analysis of [Stearic-PEG]$_p$-Hb-[mPEG]$_q$

The [Stearic-PEG]$_p$-Hb-[mPEG]$_q$ obtained from Example 3 was analyzed. The protein concentration of [Stearic-PEG]$_p$-Hb-[mPEG]$_q$ as represented by the concentration of Hb was analyzed by CO-OX SC80 Blood Gas Analyzer to be 4.5% (w/v).

Homogeneity and molecular weight of the [Stearic-PEG]$_p$-Hb-[mPEG]$_q$ were analyzed by high performance liquid chromatography (HPLC) with an absorbance reading at 280 nm. The chromatogram showed a single peak with a main peak fraction greater than 99%.

The analysis to determine the number of PEGs attached to the [Stearic-PEG]$_p$-Hb and [Stearic-PEG]$_p$-Hb-[mPEG]$_q$ was performed by TNBS (2,4,6-trinitrobenzene sulfonic acid) assay method that is known in the art (Reference: Analytical Biochemistry 14, 328-336 (1966) "Determination of Free Amino Groups in the Proteins by Trinitrobezenesulfonic Acid").

As the embodiment of Example 3 was prepared sequentially in that Hb had been treated first with an FA-PEG derivative to produce [Stearic-PEG]$_p$-Hb, a sample of this intermediate product [Stearic-PEG]$_p$-Hb was collected and assayed by the TNBS method. The number of FA-PEGs attached on Hb was 2. The [Stearic-PEG]$_p$-Hb, as per Example 3, had been treated with mPEG derivatives to produce [Stearic-PEG]$_p$-Hb-[mPEG]$_q$, which was analyzed by TNBS method. The number of total PEGs attached to Hb was 14. Therefore, it is deduced that the number of mPEGs attached to Hb was 12.

The molecular weight of the [Stearic-PEG]$_p$-Hb-[mPEG]$_q$ can now be calculated to be 135,000 Da, with the molecular weight of each PEG being 5,000 Da and the molecular weight of Hb being 65,000 Da.

Thus, the product from Example 3 can now be expressed as [Stearic-PEG]$_2$-Hb-[mPEG]$_{12}$.

Example 6: Analysis of [Stearic-PEG]$_p$-xHb-[mPEG]$_q$

The [Stearic-PEG]$_p$-xHb-[mPEG]$_q$ obtained by Example 4 was analyzed. The protein concentration of [Stearic-PEG]$_p$-xHb-[mPEG]$_q$ as represented by the concentration of Hb was analyzed by the CO-OX SC80 Blood Gas Analyzer to be 4.2% (w/v).

Homogeneity and molecular weight of the [Stearic-PEG]$_p$-xHb-[mPEG]$_q$ were analyzed by high performance liquid chromatography (HPLC) with absorbance reading at 280 nm. The chromatogram showed a single peak with a main peak fraction greater than 97%.

The number of PEGs on the [Stearic-PEG]$_p$-xHb-[mPEG]$_q$ was determined by the TNBS assay method.

As the embodiment in Example 4 was prepared sequentially in that xHb had been treated first with an FA-PEG derivative to produce [Stearic-PEG]$_p$-xHb, a sample of this intermediate product [Stearic-PEG]$_p$-xHb was collected and assayed by the TNBS method. The number of FA-PEGs attached on xHb was 2. The [Stearic-PEG]$_p$-xHb, as per Example 4, had been treated with mPEG derivatives to produce [Stearic-PEG]$_p$-xHb-[mPEG]$_q$, which was analyzed by the TNBS method. The number of total PEGs attached to Hb was 14. Therefore, it is deduced that the number of mPEGs attached to Hb was 12.

The molecular weight of the [Stearic-PEG]$_p$-xHb-[mPEG]$_q$ can now be calculated to be 135,000 Da, with the molecular weight of each PEG being 5,000 Da and the molecular weight of Hb being 65,000 Da.

Thus, the product from Examples 4 can now be expressed as [Stearic-PEG]$_2$-xHb-[mPEG]$_{12}$.

Example 7: Toxicity of [Stearic-PEG]$_2$-Hb-[mPEG]$_{12}$ in Animals

Purpose of this test was to investigate the acute toxicity of the [Stearic-PEG]$_2$-Hb-[mPEG]$_{12}$ solution within animals.

Eight-week old Sprague-Dawley male rats weighing 300±30 g were chosen and acclimated for a week. The animals were injected with 15 mL/kg of test materials, and were observed in terms of their survival for 7 days. The study period was up to 7 days, after which all animals were euthanized.

As the test material, a solution containing 4.5% of [Stearic-PEG]$_2$-Hb-[mPEG]$_{12}$ having a molecular weight of 135,000 Da, along with a pH of 7.2 was prepared.

For the test group, 5 rats received intravenously 15 mL/kg (equivalent to 675 mg/kg) of a [Stearic-PEG]$_2$-Hb-[mPEG]$_{12}$ solution via a jugular vein at a controlled rate of 0.1 mL/min using a syringe pump. For the control group, rats received 15 mL/kg of Ringers Lactate via the same route and manner. All animals were weighed and observed for behavior and survival every day for 7 days. As a result, all animals in both groups survived and were determined to be healthy at day 7. This study demonstrated the safety or non-toxicity of [Stearic-PEG]$_2$-Hb-[mPEG]$_{12}$ in rats when tested under a single intravenous bolus injection model at a dosage of 15 mL/kg (equivalent to 675 mg/kg).

Example 8: Pharmacokinetics of [Stearic-PEG]$_2$-xHb-[mPEG]$_{12}$

The purpose of this test was to investigate the pharmacokinetics of [Stearic-PEG]$_2$-xHb-[mPEG]$_{12}$ in animals. Eight-week old Sprague-Dawley male rats weighing approximately 300 g were chosen and acclimated for a week. After injection of a [Stearic-PEG]$_2$-xHb-[mPEG]$_{12}$ solution, blood samples were collected at planned time intervals and analyzed for the Hb concentration in the plasma. The Hb present in the plasma portion of the collected blood is interpreted as the concentration of [Stearic-PEG]$_2$-xHb-[mPEG]$_{12}$ retained in the intravasculature.

As the test material, a solution containing 4.5% of [Stearic-PEG]$_2$-xHb-[mPEG]$_{12}$ having a molecular weight of 135,000 Da along with a pH of 7.2 was prepared.

Three animals received 15 mL/kg (equivalent to 675 mg/kg) of [Stearic-PEG]$_2$-xHb-[mPEG]$_{12}$ intravenously via a jugular vein at a controlled rate of 0.1 mL/min using a syringe pump.

Blood samples were collected via a caudal vein at time points of 0 (immediately before injection), 1, 2, and 4 hours after injection, and at 1, 2, 3, 4, 7, and 14 days after injection. Blood samples were collected into EDTA-treated microcontainers, which were immediately centrifuged at 3,500 rpm for 15 minutes at 4° C. to separate the plasma from the precipitate. The collected plasma samples were analyzed for total Hb concentration using the CO-OX SC80 Blood Gas Analyzer. The total Hb concentration in the plasma samples indicates the presence and quantity of [Stearic-PEG]$_2$-xHb-[mPEG]$_{12}$. The [Stearic-PEG]$_2$-xHb-[mPEG]$_{12}$ concentration data was plotted on a time scale, which yielded pharmacokinetic curves.

From the pharmacokinetic data, it was determined that the intravascular half-life of 4.5% solution of [Stearic-PEG]$_2$-xHb-[mPEG]$_2$ having a molecular weight of 135,000 Da, when tested in rats at the dosage of 15 mL/kg (equivalent to 675 mg/kg), was 22 hours.

| U.S. Pat. No. Documents | | |
|---|---|---|
| 5,234,903 | August 1993 | Nho et al. |
| 5,386,014 | January 1995 | Nho et al. |
| 5,478,806 | December 1995 | Nho et al. |
| 6,844,317 | January 2005 | Winslow et al. |

-continued

| U.S. Pat. No. Documents | | |
|---|---|---|
| 7,501,499 | March 2009 | Acharya et al. |
| 7,625,862 | December 2009 | Winslow et al. |
| 7,989,414 | August 2011 | Winslow et al. |
| 8,021,858 | September 2011 | Vandegriff et al. |
| 8,377,868 | February 2013 | Winslow et al. |
| 8,609,815 | December 2013 | Vandegriff et al. |
| 9,241,979 | January 2016 | Winslow et al. |
| 10,029,001 | July 2018 | Vandegriff et al. |
| 10,080,782 | September 2018 | Abuchowski et al. |
| 10,172,950 | January 2019 | Abuchowski et al. |
| 10,821,158 | November 2020 | Malavalli et al. |

OTHER PUBLICATIONS

Walder, J. A. et al., Biochemistry, Vol 18, No 20, 4265-4270, 1979, "Diaspirins That Cross-Link β Chains of Hemoglobin: Bis(3,5-dibromosalicyl) Succinate and Bis(3,5-dibromosalicyl) Fumarate"

Habeeb, A. F. Anal Biochem 14(3):328-336, 1966 "Determination of Free Amino Groups in the Proteins by Trinitrobezenesulfonic Acid

We claim:

1. A hemoglobin derivative in which hemoglobin (Hb) or crosslinked hemoglobin (xHb) is covalently conjugated with a fatty acid-PEG (FA-PEG) derivative and an alkoxy-PEG derivative,
   wherein the Hb or xHb comprise one or more lysine residues, and an N-terminal valine residue,
   wherein the fatty-acid PEG derivative and the alkoxy-PEG derivative are each independently covalently conjugated to one of the lysine residues, or the N-terminal valine residues of the hemoglobin (Hb) or the crosslinked hemoglobin (xHb),
   wherein if the FA-PEG is covalently conjugated to the N-terminal valine residue of the Hb or xHb, then the alkoxy-PEG derivative is conjugated to one or more of the lysine residues of the Hb or xHb,
   wherein if the alkoxy-PEG is covalently conjugated to the N-terminal valine residue of the Hb or xHb, then the FA-PEG derivative is conjugated to one or more of the lysine residues of the Hb or xHb,
   wherein the crosslinked hemoglobin (xHb) is crosslinked between any two subunits of hemoglobin via bis(3,5-dibromosalicyl)fumarate or bis(3,5-dibromosalicyl)succinate,
   wherein the crosslinked hemoglobin (xHb) is intra-molecularly crosslinked between two alpha subunits or two beta subunits of hemoglobin via bis(3,5-dibromosalicyl)fumarate or bis(3,5-dibromosalicyl)succinate.

2. The hemoglobin derivative according to claim 1, wherein the alkoxy-PEG is methoxy-PEG.

3. The hemoglobin derivative according to claim 1 or 2, wherein the hemoglobin derivative is represented by the following formula (I): [FA-PEG]$_p$-Hb-[alkoxy-PEG]$_q$ where p=1~10, and q=1~20; or the following formula (II): [FA-PEG]$_p$-xHb-[alkoxy-PEG]$_q$ where p=1~10, and q=1~20.

4. The hemoglobin derivative according to any one of claims 1 to 3, wherein the FA-PEG derivative is selected from the group consisting of FA-PEG acetaldehyde, FA-PEG propionaldehyde, FA-PEG butyraldehyde, FA-PEG maleimide, FA-PEG succinimidyl carbonate, FA-PEG succinimidyl carboxymethyl, FA-PEG succinimidyl glutarate, FA-PEG succinimidyl propionate, FA-PEG succinimidyl succinate, and FA-PEG succinimidyl carboxymethyl ester.

5. The hemoglobin derivative according to any one of claims 1 to 4, wherein the alkoxy-PEG derivative is selected from the group consisting of alkoxy-PEG acetaldehyde, alkoxy-PEG propionaldehyde, alkoxy-PEG butyraldehyde, alkoxy-PEG maleimide, alkoxy-PEG succinimidyl carbonate, alkoxy-PEG succinimidyl carboxymethyl, alkoxy-PEG succinimidyl glutarate, alkoxy-PEG succinimidyl propionate, and alkoxy-PEG succinimidyl succinate.

6. The hemoglobin derivative according to any one of claims 1 to 5, wherein the fatty acid is saturated fatty acid or unsaturated fatty acid.

7. The hemoglobin derivative according to claim 6, wherein the saturated fatty acid or the unsaturated fatty acid has the number of carbons from 6 to 24.

8. The hemoglobin derivative according to any one of claims 1 to 7, wherein the PEG has molecular weight of 1,000~100,000 Da.

9. The hemoglobin derivative according to any one of claims 1 to 8, wherein the hemoglobin derivative is represented by the following formula (III) or the following formula (IV):

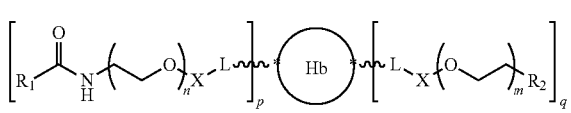

(III)

where p=1~10, q=1~20, n and m=20~2,000, $R_1$ is $C_{6-24}$ alkyl or $C_{6-24}$ alkenyl, $R_2$ is $C_{1-6}$ alkoxy, L is each independently NH from lysine residues, or N-terminal valine residues of hemoglobin (Hb), and X is each independently a divalent linker group with at least one amide, carbamate, carbonate, ester, ether, carbonyl, urethane, or succinimidyl;

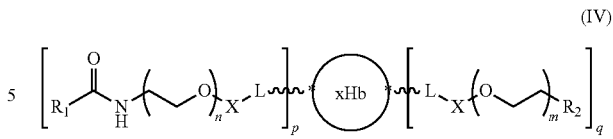

(IV)

where p=1~10, q=1~20, n and m=20~2,000, $R_1$ is $C_{6-24}$ alkyl or $C_{6-24}$ alkenyl, $R_2$ is $C_{1-6}$ alkoxy, L is each independently NH from lysine residues, or N-terminal valine residues of crosslinked hemoglobin (xHb), and X is each independently a divalent linker group with at least one amide, carbamate, carbonate, ester, ether, carbonyl, urethane, or succinimidyl.

10. The method for preparing the hemoglobin derivative according to any one of claims 1 to 9, comprising reacting hemoglobin (Hb) or crosslinked hemoglobin (xHb) with the FA-PEG derivatives and the alkoxy-PEG derivatives to provide the hemoglobin derivative covalently conjugated with FA-PEG derivatives and alkoxy-PEG derivatives.

11. The method according to claim 10, wherein said reaction is performed in a buffer solution at a temperature of 4 to 35° C. and a pH of 6 to 9.

12. A pharmaceutical composition comprising the hemoglobin derivative according to any one of claims 1 to 9 for treating a disease selected from the group consisting of hypoxia, ischemia, sepsis, sickle cell disease, retinal disease, diabetes, myocardial infarction, hemorrhagic shock, trauma, traumatic brain injury, brain stroke, tumor, and cancer.

13. A method of treating a disease selected from the group consisting of hypoxia, ischemia, sepsis, sickle cell disease, retinal disease, diabetes, myocardial infarction, hemorrhagic shock, trauma, traumatic brain injury, brain stroke, tumor, and cancer, comprising administering the hemoglobin derivative according to any one of claims 1 to 9 to a subject in need thereof.

* * * * *